United States Patent [19]

Holtkamp

[11] Plant 4,548

[45] Jun. 17, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 15,823

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African violet known by the cultivar name Connecticut having vigorous, compact growth habit; relatively large, violet colored flowers which are carried on strong erect flower stems with strong, short peduncles, and by the appearance of 7–9 flower stems with the first flash of flowers.

1 Drawing Figure

The present invention comprises a new and distinct cultivar of African violet plant, botanically known as *Saintpaulia ionantha,* and hereinafter referred to by the cultivar name Connecticut.

The new cultivar was referred to during the breeding and selection process by the designation D 210/2-80/79, and is a product of a planned breeding program. Connecticut is generally characterized by its relatively large violet flowers and compact growth habit which produces a tight bouquet of flowers over the leaves. The stems are strong and upright and carry up to 9 single flowers. The leaves are relatively large and medium green and provide a pleasant appearance with the flower bouquet. These traits in combination were not present in previously available commercial cultivars.

The new cultivar was originated from a cross made in a controlled breeding program in Isselburg, Rhineland, Germany. The female, or seed parent was a cultivar designated 26 AN/Z blue-violet single, unpatented. The male, or pollen parent was a cultivar designated B 229/11 pink single, similarly unpatented.

The new cultivar Connecticut was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Connecticut, which in combination distinguish this African violet as a new and distinct cultivar:

(1) Vigorous growth habit.

(2) Medium green leaves, round to heart-shaped, and slightly hairy.

(3) 7–9 flower stems, with up to 9 flowers on short peduncles.

(4) Large violet shaped flowers, violet in flower color.

(5) Flowers do not drop when mature, drying on the stem.

(6) Very long lasting.

(7) Compact growth habit, producing a tight flower bouquet above the leaves.

The accompanying photographic drawing shows a typical specimen plant of the new cultivar. The colors appearing in the photograph are as true as possible with color illustrations of this type.

In the following description, color references are made both to the Royal Horticultural Society color chart (RHS) and the Horticultural Colour Chart (HCC) issued by Wilson Colour Ltd. The use of both references is to provide the most accurate color values possible.

Botanical classification: *Saintpaulia ionantha,* Ramat. cv, Connecticut.

Parentage:

*Male parent.*—B 229/11 pink single.

*Female parent.*—26 AN/Z blue violet single.

Propagation: The new cultivar holds its distinguishing characteristics through successive propagations by leaf cuttings and by division of shoots.

Plant: From 8 cm. to 10 cm. tall when grown in pots, and approximately 25 cm. in diameter when fully grown.

Leaves:

*General form.*—Round to heart shaped.

*Diameter.*—55–60 mm.

*Texture.*—Soft.

*Aspect.*—Velvety, slightly shiny, hairy.

*Veins.*—Well pronounced on underside, branched out.

*Color (upperside).*—Yellow-green, RHS 147 A-B.

*Color (underside).*—More mature leaves are light green around the edges, more reddish-green to the center; young leaves on underside are dark reddish-brown and hairy.

*Petiole.*—Strong, hairy, brownish.

Flowers:

*Buds.*—Ball-shaped, 6–8 mm. in diameter before opening, dark violet in color.

*Sepals.*—Color: brown. Calyx: flat funnel. Aspect: spear-shaped, hairy. Peduncle: short, erect, hairy.

Individual flowers:

*Size.*—45–50 mm., flat.

*Color.*—Upperside: HCC 635/2 (mineral violet), with darker color (HCC 635/1) at center of flower. Underside: HCC 635/3 (mineral violet).

*Borne.*—Upright, on strong erect peduncle.

*Shape.*—Violet-shaped.

*Corolla.*—2 small petals, 3 relatively large petals 20×23 mm.; a few flowers have an additional small petal joined to the small petals, the small petals and additional petals being HCC 635/1 in color.

*Arrangement.*—On strong upright flower stems.

*Flowering time.*—7 to 8 weeks after potting the first flowers appear; full bouquet appears in 8–10 weeks.

Reproductive organs:

*Stamens.*—2 in number.

*Anthers.*—4 anther cells, RHS color 15 B (yellow orange).

*Arrangement.*—Close together.

*Filaments.*—Short bent stems, 3–4 mm. long, on flat base on round cells; light green-yellow in color on mature flowers, turning brownish.

*Styles.*—7–8 mm. long; approximately 5 mm. straight, last 3 mm. are bent (curved).

*Pollen color.*—16 B RHS (yellow orange).

Roots: Strong main root, well branched small roots; white when young, light brown when older.

Disease resistance: No disease problems to date.

General observations: Connecticut is a vigourous, compact growing violet. Nine single flowers violet in color are carried on strong erect flower stems with strong short peduncles. With the first flash of flowers, plant has 7–9 flower stems out of the center, surrounded by attractive medium green leaves. The flowers are relatively large in diameter and do not drop when mature.

I claim:

1. A new and distinct cultivar of African violet known by the cultivar name Connecticut and characterized by the combined features of vigorous, compact growth habit; relatively large, violet colored flowers which are carried on strong erect flower stems with strong, short peduncles, and by the appearance of 7–9 flower stems with the first flash of flowers.

* * * * *

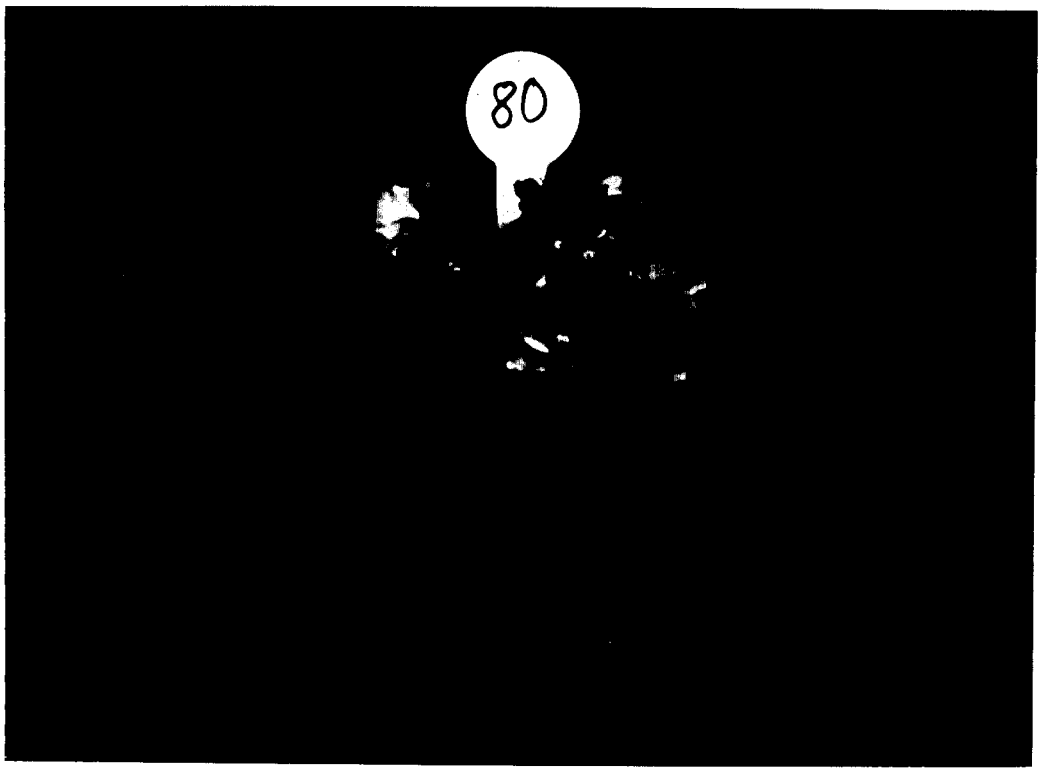
80